United States Patent [19]
Keil et al.

[11] Patent Number: 5,601,363
[45] Date of Patent: Feb. 11, 1997

[54] QUENCH SYSTEM COOLING EFFECTIVENESS METER AND METHOD OF OPERATING SAME

[75] Inventors: Gary D. Keil, Elmwood; Wayne A. Supak, Washington; Sheryl A. Tipton, East Peoria, all of Ill.

[73] Assignee: Caterpillar Inc., Peoria, Ill.

[21] Appl. No.: 255,625

[22] Filed: Jun. 9, 1994

[51] Int. Cl.⁶ .................................................. G01K 7/00
[52] U.S. Cl. .......................... 374/45; 374/114; 374/141; 374/183
[58] Field of Search .............................. 374/43, 45, 141, 374/183, 181, 114

[56] References Cited

U.S. PATENT DOCUMENTS

| | | | |
|---|---|---|---|
| 2,016,660 | 10/1935 | Weeks | 374/43 |
| 3,100,996 | 8/1963 | Roblee, Jr. | 374/183 |
| 4,016,763 | 4/1977 | Grindheim | 374/183 |
| 4,041,382 | 8/1977 | Washburn | 374/183 |
| 4,536,851 | 8/1985 | Germanton et al. | 374/183 |
| 4,563,097 | 1/1986 | Katafuchi | 374/43 |
| 4,722,611 | 2/1988 | Hultgren | 374/43 |
| 5,031,126 | 7/1991 | McCulloch et al. | 374/183 |
| 5,137,370 | 8/1992 | McCulloch et al. | 374/183 |

Primary Examiner—William A. Cuchlinski, Jr.
Assistant Examiner—Andrew Hirshfeld
Attorney, Agent, or Firm—R. Carl Wilbur

[57] ABSTRACT

A quench system cooling effectiveness meter including a reference sensor and a measurement sensor is disclosed. The reference sensor and the measurement sensor are included in a resistance bridge. The amount of heat that can be removed by the quench system from the measurement sensor is recorded to determine the cooling effectiveness of the quench system. The meter can be moved to different locations within the quench system to measure cooling variations within the system as a function of location.

27 Claims, 3 Drawing Sheets

QUENCH SYSTEM COOLING EFFECTIVENESS METER AND METHOD OF OPERATING SAME

FIELD OF THE INVENTION

The present invention relates generally to an apparatus for quantifying the effectiveness or cooling power of a quench system, and more specifically to a self contained quench device that measures a localized cooling effect of the quench system.

BACKGROUND OF THE INVENTION

When articles such as metal parts are formed, it is sometimes desirable to harden the parts to improve durability and wear characteristics. One way to harden the part is to immerse the part in a quench system immediately after heating the part to the desired heat treat temperature. Many different types of media can be used in the quench system, including oil or water, or aqueous polymer solutions, depending on a variety of factors including the material from which the part is made and the desired hardness and microstructural characteristics of the part.

It is desirable for the quench system to provide uniform cooling and for the cooling to be repeatable. Nonuniform cooling can result in varying degrees of hardness, quench cracks, increased distortion and other problems. There are many factors that contribute to nonuniformity of cooling within the quench system. These may include the tank shape and depth, flow rates within the system and impurities in the system fluid.

Typically, to determine the effectiveness or cooling power of a particular quench system, it has been necessary to quench one or more parts or samples in various areas of the quench system, then cut these parts through one and sometimes several sections to thoroughly analyze hardness and microstructure. However, this procedure is extremely labor intensive and destroys what might otherwise have been a usable part. Moreover, the test only determines the effectiveness at one point in time. It cannot actively monitor the effectiveness of a quench system.

There is one type of quench cooling effectiveness apparatus known in the prior art. That type of apparatus is generally disclosed in U.S. Pat. No. 4,563,097 (hereinafter referred to as "the '097 patent"), entitled "Method of Evaluating Cooling Performance of Heat Treatment Agent And Apparatus Therefor". The '097 patent discloses an apparatus having a single resistance temperature detector ("RTD"). This apparatus applies varying current levels to the RTD which causes the RTD to be heated to different temperature levels. Because a temperature/resistance relationship is known for the RTD, the apparatus can determine the RTD temperature as a function of the voltage applied to the RTD and a measured current through the RTD.

In the '097 patent, the RTD sensor is installed into a quench system and the RTD temperature is varied to produce a dissipated heat v. temperature curve for that particular quench media. The effectiveness of different quench media can thereby be analyzed. For example, one particular quench medium may dissipate heat most effectively for parts cooling to 650 degrees Centigrade while another fluid may be more effective on parts cooling to 550 degrees Centigrade. From the curves produced for the various quench media, the most effective fluid can be selected and utilized for a particular part.

However, an apparatus such as that disclosed in the '097 patent suffers from several disadvantages. For example, the sensor itself is repeatedly heated to relatively hot temperatures to simulate the temperature of the parts to be quenched. The repeated heating and cooling of the sensor causes the sensor to have a short life span and the sensors often fail. Another disadvantage of the disclosed apparatus is that it generally must be installed through a wall of the quench tank. Moreover, the apparatus cannot be quickly moved within the tank to determine effectiveness of different positions in the tank. The apparatus also does not simulate the shape of a typical part to be quenched. Thus, cooling characteristics of the apparatus may be significantly different from those of an actual part. Fluid flow in the quench system can differ significantly once actual parts are placed in the system, and since the apparatus isn't portable, it can't easily be placed between parts to determine this effect. For at least these reasons, the quench cooling effectiveness apparatus disclosed in the '097 patent may not be a good predictor of actual quench characteristics experienced by actual parts.

The present invention is directed toward overcoming one or more of the disadvantages associated with the prior art quench cooling effectiveness apparatus.

SUMMARY OF THE INVENTION

The present invention relates to an apparatus for quantifying the effectiveness of a quench system. A preferred embodiment of the invention includes a housing, a reference temperature sensor, a measurement sensor, and circuit means connected to said reference temperature sensor and said measurement sensor for responsively producing a signal that is a function of the cooling rate of the quench system.

Another aspect of the present invention provides a method for determining the effectiveness of a quench system using a quench quantification meter. The quench quantification meter includes a quench reference temperature sensor, a measurement sensor, a control circuit, a data storage device, and a resistance bridge. The method includes the steps of placing the quench meter in said quench system, applying a voltage to the resistance bridge, the voltage being a function of a resistance of the quench system temperature sensor and a resistance of said cooling rate sensor, and recording said voltage in said data storage device.

Other aspects and advantages of the present invention will become apparent upon reading the detailed description of the preferred embodiment in connection with the drawings and appended claims.

DETAILED DESCRIPTION OF THE PREFERRED EMBODIMENT

The following detailed description of the preferred embodiment discloses the best mode and preferred embodiment of the invention. Although the detailed description discloses a preferred embodiment it should be recognized that the present invention is not limited to the single embodiment disclosed herein. On the contrary, the present invention includes all other embodiments and equivalents that fall within the scope of the appended claims.

Figure 1:
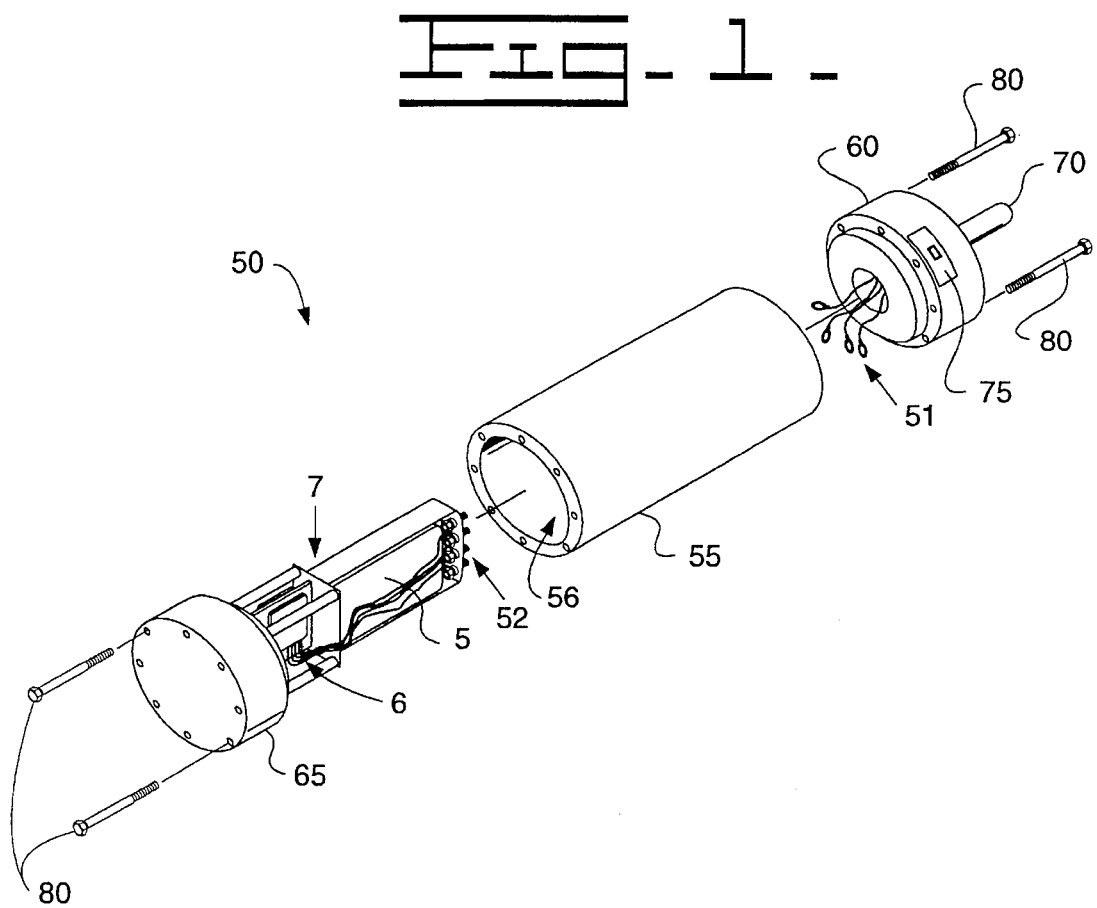
FIG. 1 is an exploded isometric view of a preferred embodiment of the present invention.

Referring first to FIG. 1, a preferred embodiment of the quench meter 50 of the present invention is shown in an exploded isometric view. The quench meter 50 includes a first end cap 60, a second end cap 65, and a housing body 55. The first end cap 60 and the second end cap 65 can be securely fastened to the housing body 55 with bolts 80 to form a liquid tight cavity 56. As shown in the figure, when the first and second end caps 60, 65 are fastened to the housing body 55, a preferred embodiment of the quench meter takes the form of a cylinder. However, the present invention is not limited to a cylindrical shape, and may take other different shapes such as a gear or crankshaft shape.

In a preferred embodiment, it is desirable for the quench meter to be smaller than the quench tank so that the quench meter may be placed in various positions within the quench tank to measure the cooling rate at those locations. In this manner the quench meter can measure variations in cooling effect within the quench tank and allow the capability to map the cooling effectiveness of a quench according to position within the quench system.

Also, it is desirable for the quench meter to approximate the size of a piece part. Then, it is possible to insert the quench meter in the quench tank in place of an actual part to measure the actual cooling effect when parts are present in the system. Also, when the quench meter is approximately the size of a piece part, it will create similar flow disturbances within the tank, thereby better approximating the actual cooling effect of the quench system on piece parts. Also, the quench meter measurement sensor can be attached to an actual part with connections running to the quench meter. Or for large parts, the quench meter could be embedded into a test part with the measuring sensor(s) located in areas of interest.

A control circuit holder 7 is preferably fastened to a surface of an end cap that forms a part of the liquid tight cavity 56. In a preferred embodiment the control circuit holder 7 is fastened to the second end cap 65. The control circuit holder 7 holds a control circuit 6, which includes a power source 5. The control circuit holder 7, control circuit 6, and the power source 5 are inserted in the liquid tight cavity 56 when the second end cap 65 is fastened to the housing body 55.

Attached to the first end cap 60 is a reference sensor 70 and a measurement sensor 75. Although a preferred embodiment of the present invention includes one measurement sensor 75, in some applications two or more sensors might be desirable. The present invention is not limited to a device having a single measurement sensor 75, but instead includes devices having multiple measurement sensors and other embodiments that fall within the scope of the appended claims. For example, multiple sensors could be used to either give an average cooling effect or an independent cooling effect as a function of location.

The reference sensor 70 is preferably positioned on an end of the first end cap 60. However, the reference sensor 70 might also be placed on other locations of the quench meter 50. In a preferred embodiment, the reference sensor 70 includes a resistance temperature detector ("RTD"). The reference sensor 70 is preferably selected so that it is relatively insensitive to self heating or flow effects and thus accurately measures the ambient temperature of the fluid in the quench system.

The measurement sensor 75 is fixed to a surface of the first end cap 60. However, prelocation of the measurement sensor 75 can be easily changed and it can be positioned anywhere on the outside of the meter or attached on a piece part in the quench system. The measurement sensor 75 is selected so that it develops heat when an electrical current is applied. The measurement sensor 75 is preferably located on the first end cap 60 in a manner so that the first end cap 60 generally does not absorb heat generated by the measurement sensor 75. In this manner, any heat generated by the measurement sensor 75 must be absorbed by, or dissipated into, the fluid in the quench media. As is described more fully below, this allows the control circuit 6 to produce a signal that is a function of the quench system's ability to remove heat from a piece part, i.e. to measure the quench system cooling effect.

The reference sensor 70 and the measurement sensor 75 are connected to the control circuit 6 through electrical connectors 51. The electrical connectors 51 are attached to a terminal strip 52 preferably located on the control circuit holder 7. Once the second end cap 65 has been fastened to the housing body 70 the electrical connectors 51 are connected to the terminal strip 52. The terminal strip 52 is connected to the control circuit 6. In this manner, as described more fully below, the sensors 70, 75 are included in a resistance bridge 21 of the control circuit 6.

Figure 2:
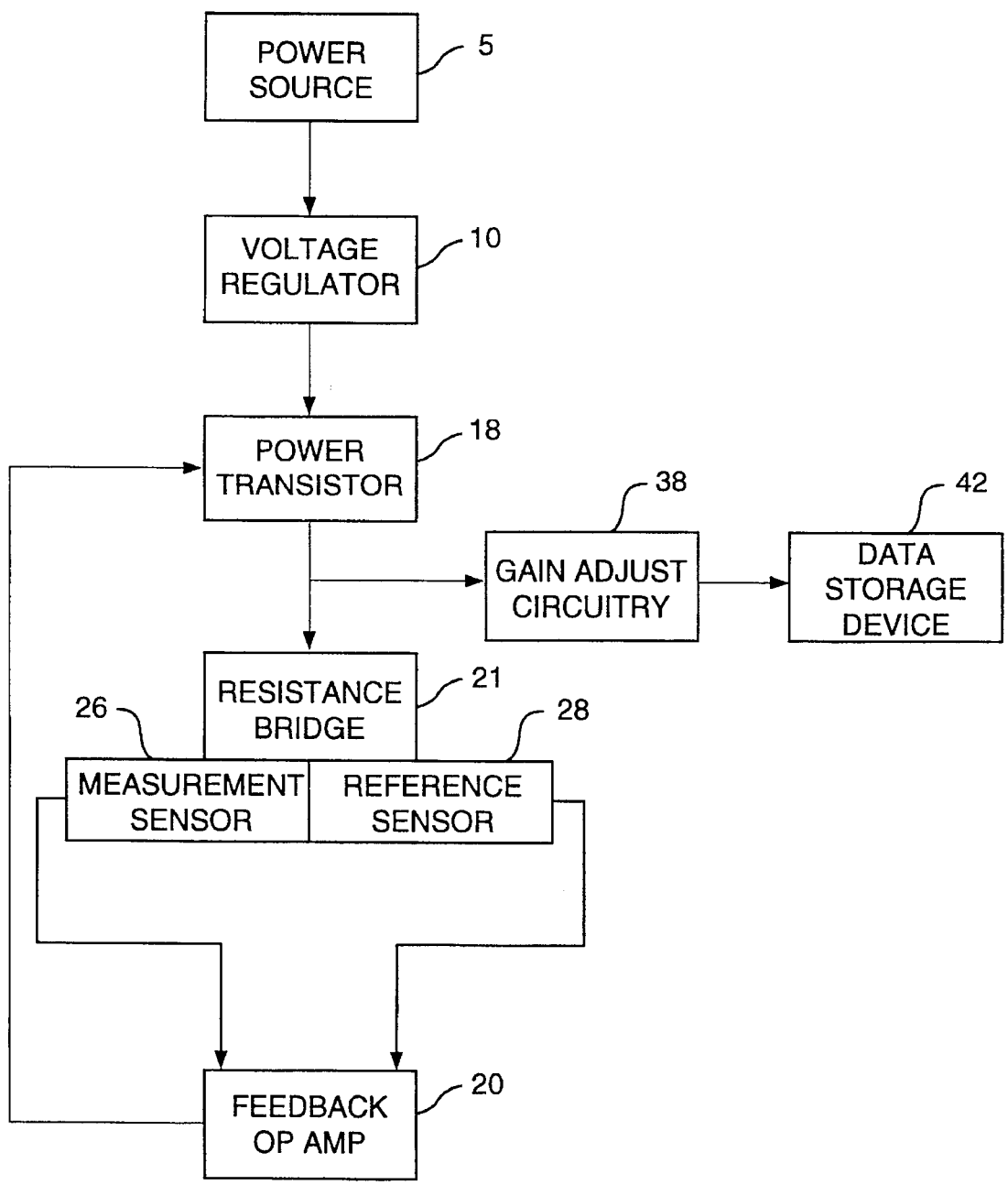
FIG. 2 is a functional block diagram of a preferred embodiment of the control circuitry used in connection with the present invention.

Referring now to FIG. 2, a functional block diagram of the control circuit 6 used in connection with a preferred embodiment of the present invention is shown. The first block 5 represents a power source for the control circuit 6. The power source is connected to a voltage regulator represented by block 10 which maintains a regulated supply voltage. The regulated supply voltage is an output to a power transistor represented by block 18. The power transistor 18 controls the application of current to a resistance bridge 21. The resistance bridge 21 includes a resistance value of both the reference sensor 70 and the measurement sensor 75.

An output of the resistance bridge 21 is two voltage levels. The first voltage level is the voltage across the measurement sensor resistance 26 and the second voltage level is the voltage level across the reference sensor resistance 28. Those voltage levels are fed into a feedback op-amp represented by block 20. The output of the feedback op-amp 20, in turn, controls the voltage applied to the power transistor 18 which controls current flowing to the resistance bridge 21. As is explained more fully below, the feedback op-amp 20, in this manner, adjusts the heat generated by the measurement sensor 75. The quench system then removes the generated heat. The ability of the quench system to remove heat, in part, determines the amount of current that the power transistor 18 applies to the resistance bridge 21.

The output of the power transistor 18 therefore is a measure of the cooling effect of the quench system. That output can be stored by a data storage device 42 for later analysis. However, first the output must be scaled to an appropriate voltage level prior to being stored in the data storage device 42. Thus, the power transistor output is first scaled by gain adjustment circuitry represented by block 38. The output of block 38 is then stored by the data storage device 42.

Figure 3:
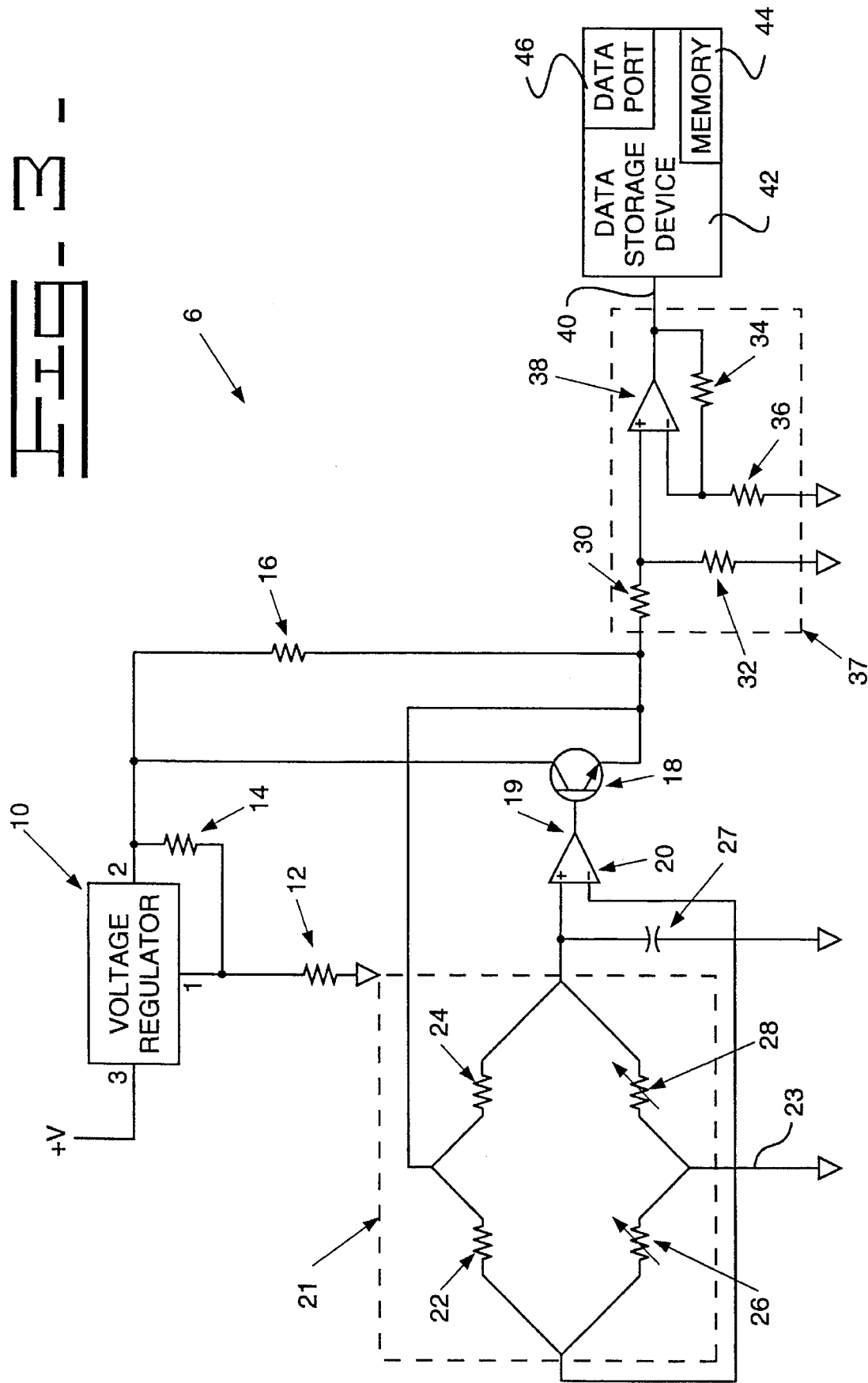
FIG. 3 is a schematic diagram of a control circuit used in a preferred embodiment of the present invention.

Referring now to FIG. 3, a schematic circuit diagram of a preferred embodiment of the control circuit 6 is shown. The control circuit 6 generally conforms to the functional block diagram shown in FIG. 2.

The control circuit 6 is powered by a power supply V+. In a preferred embodiment the power supply is a battery, which enables the circuit and power supply V+ to be contained within the liquid tight cavity 56 of the quench meter 50.

Although a battery is used in a preferred embodiment, other power supplies could be used without deviating from the spirit and scope of the present invention as defined by the appended claims.

The power supply voltage V+ is applied to a voltage regulator 10. Resistors 12, 14 are connected to the voltage regulator 10 in a known manner to adjust the output voltage at output pin 2 to a desired level. The output of the voltage regulator is connected to the collector of a power transistor 18 and to a resistor 16. Current flows through the resistor 16 and through a resistor bridge 21 to ground 23.

The resistor bridge preferably comprises four resistors 22,24,26,28. Two resistors 22,24 are balancing resistors and are selected as a function of the other resistance values in the bridge. Resistor 26 represents the resistance of the measurement sensor 75. In a preferred embodiment the resistance of the sensor is approximately 50 ohms at 70 degrees fahrenheit. However, it should be recognized that other resistance values can be readily and easily substituted without deviating from the spirit and scope of the present invention. Resistor 28 represents the resistance of the reference sensor 70.

Electrical current flows through two branches of the resistance bridge 21. A first branch includes resistors 22,26 and a second branch includes resistors 24, 28. The resistance values for the resistors 22, 24, 26, 28 comprising the resistance bridge 21 are selected so that the voltage level across the reference sensor resistance 28 should normally be slightly higher than the voltage across the measurement sensor resistance 26. This slight imbalance in the resistance bridge 21 will cause a DC voltage normally to be applied to the resistance bridge, as is described more fully below. The voltage levels across the measurement sensor 75 will change, however, because the resistance value for the measurement sensor 75 changes with the cooling effect of the quench system. As the cooling effect of the quench reduces the temperature of the measurement sensor 75, its resistance value 26 decreases. The voltage across the resistance 26 then becomes less than the voltage across the reference sensor resistance 28.

The voltages across the reference sensor resistance 28 and the measurement sensor resistance 26 are inputs to the feedback op-amp 20. The voltage across the reference sensor resistance 28 is connected to capacitor 27, which is connected to ground 23. The capacitor 27 removes high frequency oscillations from the input voltage and tends to create a steady state DC voltage at the input to the feedback op-amp 20. The voltage across the capacitor 27 is then fed into the positive input of the feedback op-amp 20. The voltage across the measurement sensor resistance 26 is an input to the negative input of the feedback op-amp 20. When the voltage at the positive input of the feedback op-amp 20 exceeds the voltage at the negative input, the feedback op-amp 20 produces a positive voltage at its output 19.

The output 19 of the feedback op-amp 20 is connected to the base of the power transistor 18. When the feedback op-amp 20 produces a positive voltage output, current flows to the base of the power transistor 18 turning the transistor on. Electrical current then flows from the collector to emitter of the power transistor 18 and to the resistance bridge 21.

The reference sensor 70 is preferably designed so that increasing current flow through the sensor does not produce a significant heating effect. The measurement sensor 70 is preferably designed so that increasing the current flow through the sensor will produce a heating effect. If the quench system cannot remove the additional heat created by the measurement sensor 75, then the measurement sensor 75 will increase in temperature. The increased temperature will cause the resistance value 26 of the measurement sensor 75 to increase. The voltage across the measurement sensor resistance 26 then will increase. The increasing voltage at the negative input of the feedback op-amp will reduce the voltage output 19 of the op-amp. Thus, the power transistor 18 will reduce current flow to the resistance bridge 21 thereby decreasing the heat produced by the measurement sensor 75. When the quench system is able to remove the heat generated by the measurement sensor 75, then the input at the feedback op-amp 20 will balance to produce a different steady state output. In this manner, as cooling effect changes, the feedback op-amp output changes and thus the voltage across the power transistor changes. The voltage across the power transistor is therefore a measure of cooling effect.

In contrast, when the cooling effect of the quench system removes more heat than the measurement sensor 75 is producing the measurement sensor temperatures will decrease, decreasing the voltage across the measurement sensor 75. The decreased voltage at the negative input to the feedback op-amp 20 will therefore cause the feedback op-amp 20 to produce a positive voltage output. This in turn increases current flowing through the power transistor 18, which increases current to the measurement sensor 75. The increased current then produces heat in the measurement sensor 75 until its resistance again causes the voltages at the inputs to the feedback op-amp 20 to be balanced at a new, higher steady state level.

The current applied by the power transistor 18 to the resistance bridge 21 is therefore a measure of the heat being produced in the measurement sensor 75 and dissipated by the quench system. By measuring the voltage at the output of the power transistor 18 it is possible to determine the voltage that the power transistor 18 is applying to the resistance bridge and thus, the times when additional heating is required by the measurement sensor 75 to maintain the balance of the resistance bridge 21. This measurement is therefore an indication of the cooling effectiveness of the quench system in the area around the measurement sensor 75.

The control circuit 6 includes gain adjustment circuitry 37 to adjust the voltages of the power transistor 18 output. As is known in the art, by selecting appropriate resistors 30,32, 34,36 in connection with an op-amp 38 the input voltage at resistor 30 can be proportionally amplified or divided. In a preferred embodiment of the present invention, the resistors 30,32,34,36 are selected to reduce the voltage range output at line 40 to the range of 0–5 volts. As is known in the art, other resistance values could be readily and easily selected to scale the voltage output at line 40 to a different range. The range is selected to be compatible with the particular data storage device 42 that is used.

In a preferred embodiment, a data storage device 42 periodically stores the values of the gain adjustment circuitry output in memory 44. Data storage devices are well known in the art. It would be a mechanical step for those skilled in the art to use such a device in connection with the present invention. Thus, they are not described further herein.

A data port 46 is provided in connection with the data storage device 42. Once data have been collected, a personal computer or other such device (not shown) can be connected to the data port 46 to download the collected data. The data can then be analyzed to determine the cooling effectiveness of the quench system.

We claim:

1. An apparatus for measuring the effectiveness of a quench system, comprising in combination:

a fluid tight housing;

a reference temperature sensor attached to said housing;

a measurement temperature sensor attached to said housing; and circuit means connected to said reference temperature sensor and said measurement sensor for producing a current through said measurement sensor thereby causing said measurement sensor to produce heat, for controlling said current to produce a desired temperature differential between said measurement sensor and said reference sensor, and for producing a signal that is a function of the cooling effectiveness of the quench system, wherein said circuit means is installed within said fluid tight housing.

2. The apparatus according to claim 1, including:

a data storage device connected to said circuit means;

wherein said data storage device periodically stores a value of said signal in said data storage device; and wherein said data storage device is sealed within said fluid tight housing.

3. The apparatus according to claim 2, wherein said reference temperature sensor varies an electrical resistance as a function of temperature.

4. The apparatus according to claim 2, wherein said measurement sensor varies an electrical resistance as a function of temperature.

5. The apparatus according to claim 4, wherein said circuit means produces an electrical voltage applied to said measurement sensor; and wherein said measurement sensor responsively produces said heat.

6. The apparatus according to claim 5, wherein said electrical voltage is applied to said measurement sensor as a function of a difference between a temperature of said reference temperature sensor and a temperature of said measurement sensor.

7. The apparatus according to claim 5, wherein said electrical voltage is applied to said measurement sensor as a function of the electrical resistance of said reference temperature sensor and the electrical resistance of said measurement sensor.

8. The apparatus according to claim 7, wherein said reference temperature sensor produces negligible heat as a result of an applied electrical current.

9. The apparatus according to claim 7, wherein the electrical resistance of said reference temperature sensor is greater than the resistance of said measurement sensor when said measurement and said reference sensors are at 70 degrees Fahrenheit.

10. The apparatus according to claim 9, wherein said circuit means includes a resistor bridge, said resistor bridge including said reference temperature sensor and said measurement sensor.

11. The apparatus according to claim 10, wherein said periodically stored values of said signal are downloadable to an external computer through said data port.

12. The apparatus according to claim 1, wherein said reference temperature sensor varies an electrical resistance as a function of temperature.

13. The apparatus according to claim 12, wherein said measurement sensor varies an electrical resistance as a function of temperature.

14. The apparatus according to claim 1, wherein the external dimensions of said liquid tight housing are smaller than a quench tank of said quench system.

15. The apparatus according to claim 1, including:

a power source connected to said circuit means, said power source being installed within said fluid tight housing.

16. The apparatus according to claim 15, wherein said apparatus is completely immersible in a quench bath of said quench system.

17. An apparatus for measuring the effectiveness of a quench system, comprising in combination:

a housing having a sealable internal cavity and an exterior surface;

an electrical circuit installed in said sealable internal cavity;

a first resistance temperature detector external to said sealable internal cavity and electrically connected to said electrical circuit;

a second resistance temperature detector attached to said housing exterior surface and electrically connected to said electrical circuit;

wherein the resistance of said first resistance temperature detector is a function of an ambient temperature of the quench system;

wherein the resistance of said second resistance temperature detector is a function of the cooling effect of said quench system;

wherein said electrical circuit produces an electrical current through said second resistance temperature detector causing said second resistance temperature detector to produce heat;

wherein said electrical circuit controls said electrical current to maintain a desired temperature differential between said first and second resistance temperature detectors; and wherein said electrical circuit produces an electrical signal that is a function of said cooling effect of said quench system.

18. The apparatus according to claim 17, wherein said electrical circuit includes a resistance bridge, said resistance bridge including said first and second resistance detectors.

19. The apparatus according to claim 18, wherein said electrical circuit produces an electrical voltage applied to said resistance bridge, said electrical voltage producing said heating of said second resistance temperature detector.

20. The apparatus according to claim 19, wherein the electrical voltage applied to said resistance bridge is a function of a difference between the temperature of said first resistance temperature detector and the temperature of said second resistance temperature detector.

21. The apparatus according to claim 19, wherein said electrical voltage applied to said resistance bridge is a function of the resistance of said first resistance temperature detector and the resistance of said second resistance temperature detector.

22. The apparatus according to claim 21, including:

a data storage device connected to said electrical circuit and installed in said sealable internal cavity; and wherein said data storage device stores a plurality of said electrical signal values.

23. The apparatus according to claim 22, including downloading means connected to said data storage device for permitting said stored electrical signal values to be downloaded to an external computer.

24. The apparatus according to claim 23, wherein the electrical resistance of said first resistance temperature detector exceeds the electrical resistance of said second resistance temperature detector at an equivalent temperature.

25. A method for determining the effectiveness of a quench system using a quench system effectiveness meter, the quench system effectiveness meter including a fluid tight housing, a reference temperature sensor, a measurement temperature sensor, a control circuit installed within said fluid tight housing and connected to said reference temperature sensor and said measurement temperature sensor, a memory device, and a power supply connected to said control circuit, the method comprising the steps of:

placing said quench meter in said quench system;

applying a voltage to said measurement sensor and said reference sensor;

controlling said voltage to maintain a desired temperature differential between said measurement sensor and said reference sensor, said voltage causing said measurement sensor to produce heat;

recording said voltage in said memory device; and correlating said voltage to a cooling effect of said quench system.

26. A self contained, immersible apparatus for measuring the effectiveness of a quench system, comprising in combination:

a fluid tight housing;

a reference temperature sensor;

a measurement temperature sensor;

circuit means connected to said reference temperature sensor and said measurement sensor for producing current through said measurement sensor thereby causing said measurement sensor to produce heat, and for controlling said current to maintain a desired temperature differential between said measurement sensor and said reference sensor, wherein said current is a function of the cooling effectiveness of the quench system, and wherein said circuit means is installed within said fluid tight housing;

a power source connected to said circuit means and installed within said fluid tight housing; and a memory device for recording a value of said current.

27. A method for determining a cooling effectiveness profile of a quench system using a quench effectiveness meter which includes a fluid tight housing, a reference temperature sensor, a measurement temperature sensor, an electrical circuit connected to said reference temperature sensor and said measurement sensor, said electrical circuit producing a voltage across said measurement and reference sensors thereby producing heat in said measurement sensor, said electrical circuit controlling said voltage to maintain a desired temperature differential between said measurement and said reference sensors, said electrical circuit being installed within said fluid tight housing, and memory means for recording said signal, said method comprising the steps of:

placing the quench effectiveness meter in a first location within a quench tank;

moving the quench effectiveness meter sequentially to a plurality of predetermined locations within the quench tank, the quench effectiveness meter remaining at each predetermined location for a predetermined time period; recording data corresponding to said voltage at said plurality of predetermined locations;

downloading said data; and correlating said downloaded data to each of said plurality of predetermined locations.

* * * * *